(12) United States Patent
McLaughlin

(10) Patent No.: US 10,251,734 B1
(45) Date of Patent: Apr. 9, 2019

(54) SALIVA MANAGEMENT SYSTEM

(71) Applicant: Douglas McLaughlin, Newburgh, NY (US)

(72) Inventor: Douglas McLaughlin, Newburgh, NY (US)

( * ) Notice: Subject to any disclaimer, the term of this patent is extended or adjusted under 35 U.S.C. 154(b) by 0 days.

(21) Appl. No.: 15/646,256

(22) Filed: Jul. 11, 2017

(51) Int. Cl.
*A61C 17/00* (2006.01)
*A61C 17/02* (2006.01)
*A61M 11/00* (2006.01)

(52) U.S. Cl.
CPC .............. *A61C 17/02* (2013.01); *A61C 17/00* (2013.01); *A61M 11/00* (2013.01)

(58) Field of Classification Search
CPC ........ A61M 11/00; A61C 17/02; A61C 17/00; A61C 13/267; A61C 17/005; A61C 17/16
See application file for complete search history.

(56) References Cited

U.S. PATENT DOCUMENTS

| | | | | |
|---|---|---|---|---|
| 3,199,510 A | * | 8/1965 | Sinai | A61C 17/02 128/200.14 |
| 4,524,790 A | * | 6/1985 | Kelley | A61C 7/00 222/324 |
| 4,793,339 A | * | 12/1988 | Matsumoto | B05B 17/0623 128/200.16 |
| 5,078,129 A | | 1/1992 | Kleinberg | |
| 5,558,518 A | * | 9/1996 | Bab | A61C 17/02 433/216 |
| 6,652,481 B1 | | 11/2003 | Brown | |
| D616,152 S | | 5/2010 | Manzo | |
| 8,979,823 B2 | | 3/2015 | Podmore | |
| 2008/0272153 A1 | | 11/2008 | Hochstadter | |
| 2013/0025607 A1 | | 1/2013 | Altounian | |
| 2013/0122453 A1 | * | 5/2013 | Paxton | A61B 1/24 433/29 |
| 2015/0044628 A1 | * | 2/2015 | Flyash | A61C 19/066 433/27 |

FOREIGN PATENT DOCUMENTS

WO     2012109166 A2     8/2012

* cited by examiner

*Primary Examiner* — Nathan R Price
*Assistant Examiner* — Melissa A Snyder
(74) *Attorney, Agent, or Firm* — Kyle A. Fletcher, Esq.

(57) ABSTRACT

The saliva management system is a device that can be worn at night while sleeping to help alleviate dry mouth syndrome. The device utilizes a wind-up timer to periodically release a burst of water mist directly into the mouth, under the tongue. The water comes from a reservoir located within the housing of the saliva management system. The device comprises teeth clips and a strap to hold it in place. A built-in, finger-operated pump pressurizes the water to force it out of the reservoir via misting nozzles. A valve release is included to allow easier draining and cleaning of the device.

16 Claims, 3 Drawing Sheets

SALIVA MANAGEMENT SYSTEM

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the fields of personal health and personal hygiene, more specifically, a device for use while sleeping, which helps alleviate dry mouth syndrome.

SUMMARY OF INVENTION

The saliva management system is a device that can be worn at night while sleeping to help alleviate dry mouth syndrome. The device utilizes a wind-up timer to periodically release a burst of water mist directly into the mouth, under the tongue. The water comes from a reservoir located within the housing of the saliva management system. The device comprises teeth clips and a strap to hold it in place. A built-in, finger-operated pump pressurizes the water to force it out of the reservoir via misting nozzles. A valve release is included to allow easier draining and cleaning of the device.

Dry mouth syndrome, also known as dry mouth or xerostomia, is a condition characterized by an unusually dry mouth. Dry mouth syndrome may result from a change in the composition of saliva, as a side effects of medications, from breathing through one's mouth, or it may not have an identifiable cause. Dry mouth syndrome may result in a higher incidence of tooth decay, altered taste sensation, oral infections, more sores, difficulty in wearing dentures, and many other signs and symptoms.

An object of the invention is to help alleviate dry mouth syndrome by providing a periodic burst of water mist directly into a user's mouth.

Another object of the invention is to provide a device that can be worn at night while sleeping.

Yet another object of the invention is to provide the device with a self-contained source of water.

Another object of the invention is to allow the user to pressurize an internal water reservoir using a finger pump built into the device.

These together with additional objects, features and advantages of the saliva management system will be readily apparent to those of ordinary skill in the art upon reading the following detailed description of the presently preferred, but nonetheless illustrative, embodiments when taken in conjunction with the accompanying drawings.

In this respect, before explaining the current embodiments of the saliva management system in detail, it is to be understood that the saliva management system is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the saliva management system.

It is therefore important that the claims be regarded as including such equivalent construction insofar as they do not depart from the spirit and scope of the saliva management system. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description. As used herein, the word "or" is intended to be inclusive.

Figure 1:
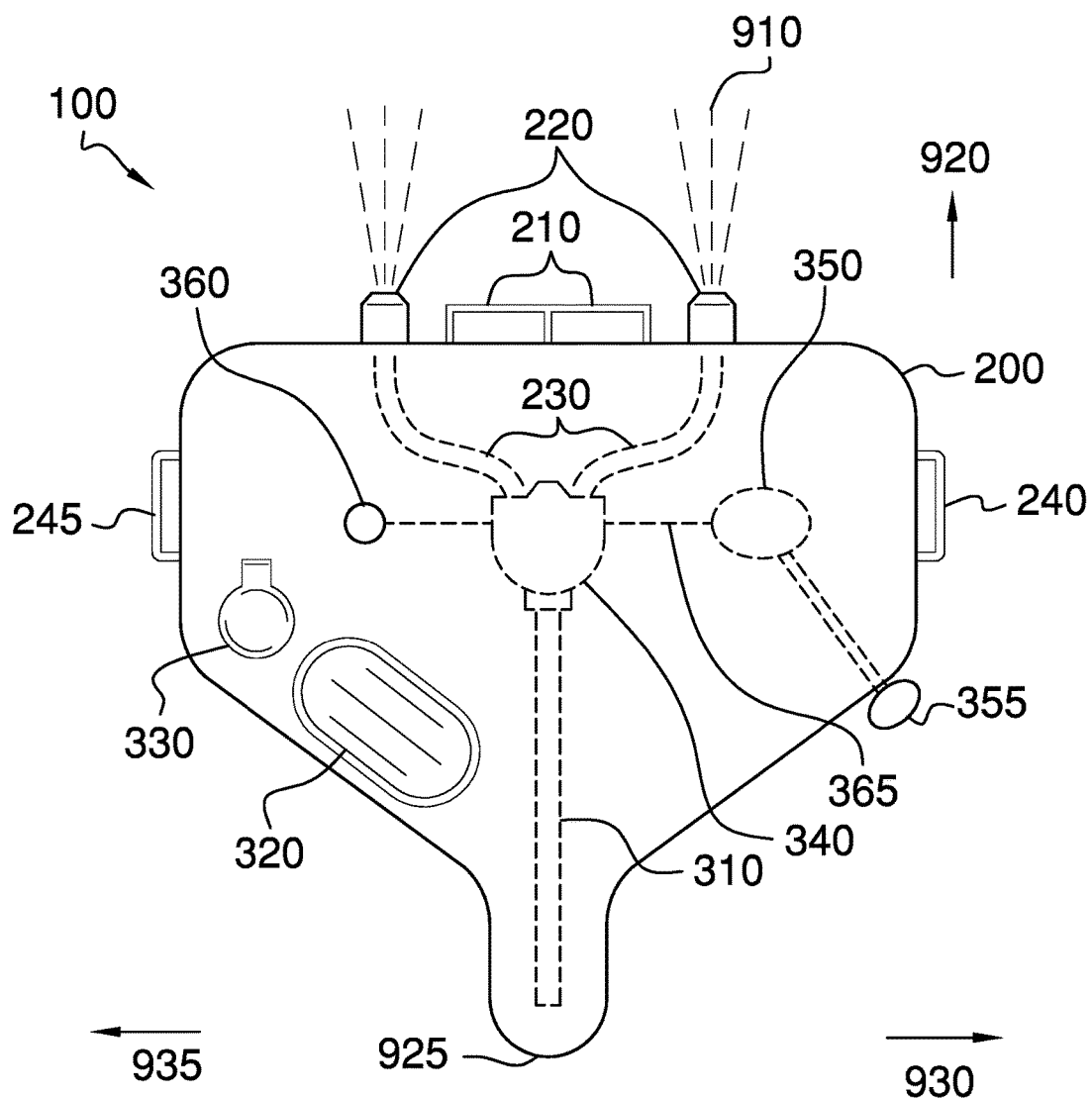
FIG. 1 is a top view of an embodiment of the disclosure.
Figure 2:
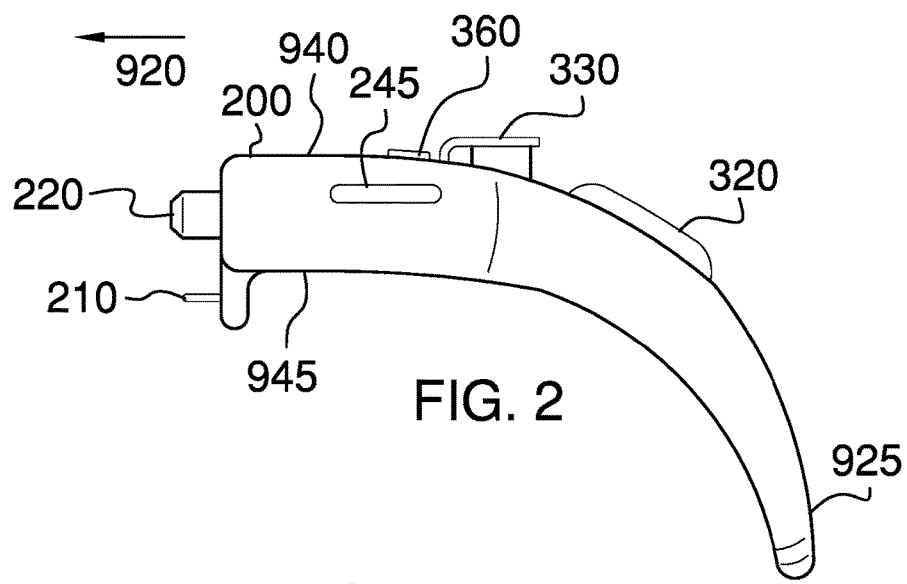
FIG. 2 is a side view of an embodiment of the disclosure.
Figure 3:
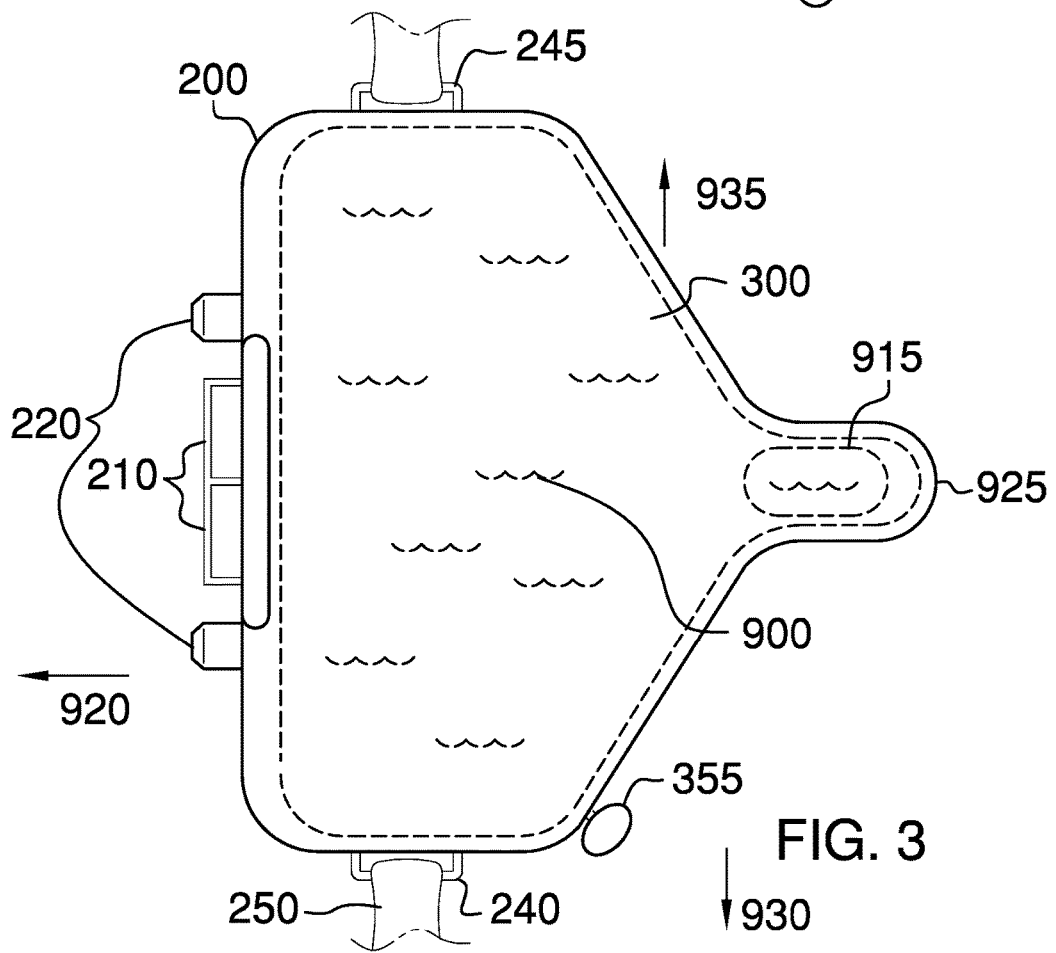
FIG. 3 is a bottom view of an embodiment of the disclosure.
Figure 4:
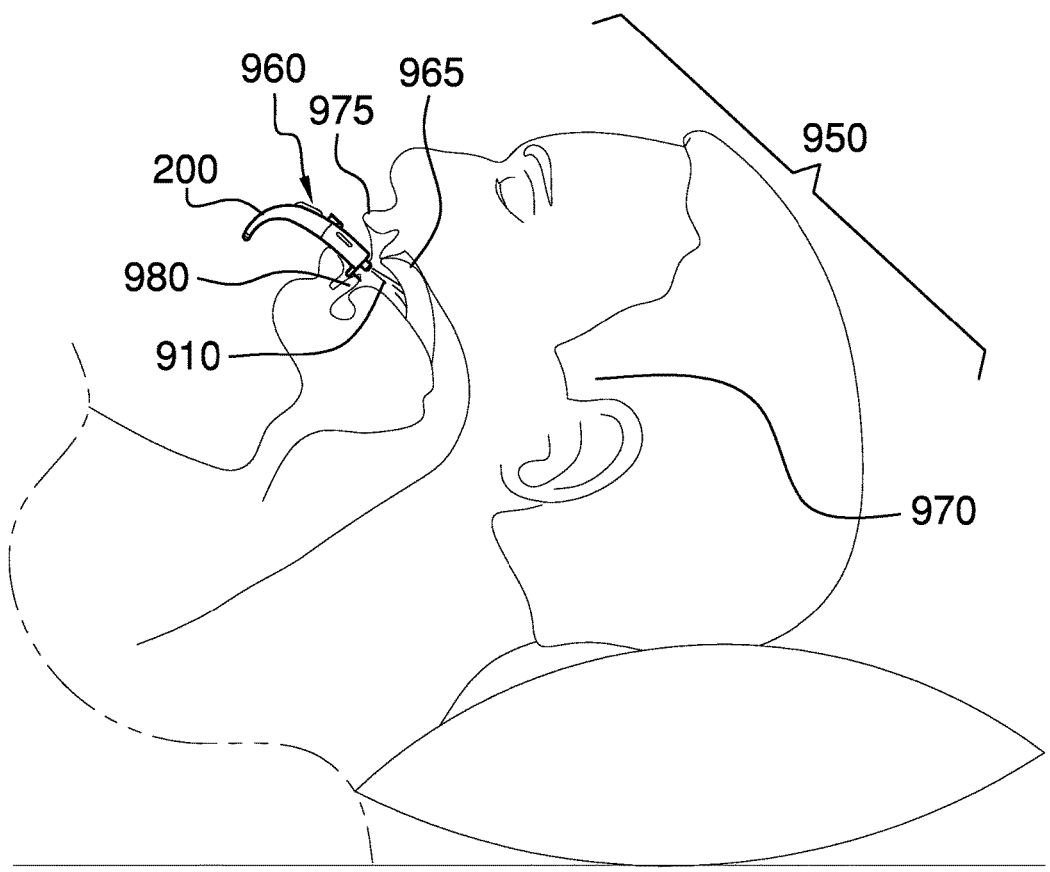
FIG. 4 is a side view of an embodiment of the disclosure while in use.

Detailed reference will now be made to a first potential embodiment of the disclosure, which is illustrated in FIGS. 1 through 4.

The saliva management system 100 (hereinafter invention) comprises a housing 200, a water reservoir 300, one or more spray nozzles 220, one or more teeth clips 210, a valve 340, a valve timer 350 and a finger pump 320. The invention 100 is intended to be worn by a user 950 while sleeping and will periodically spray a mist 910 of water 900 into a mouth 960 of the user 950 to alleviate a condition called dry mouth syndrome.

The housing 200 is an enclosure for the invention 100. The housing 200 is adapted to be worn by the user 950. Specifically, the housing 200 has a front side 920 that comes into contact with the mouth 960 of the user 950. The one or more spray nozzles 220 and the one or more teeth clips 210 are mounted on the front side 920 of the housing 200. The housing 200 has a top surface 940 and a bottom surface 945. Both the top surface 940 and the bottom surface 945 curve downward as they progress towards a rear point 925 of the housing 200. Note that throughout this document directions are given from the perspective of the user 950 while the user 950 is seated upright with the invention 100 placed in the mouth 960 of the user 950. Viewed from a side, the housing 200 is thin enough to be inserted into the mouth 960 of the user 950. Specifically, the housing 200 has a maximum thickness at the front side 920 of no more than 50 mm. The distance from the top surface 940 to the bottom surface 945 may narrow at the rear point 925. Because of this, the housing 200 may appear to be half-crescent shaped when viewed from a side. The housing 200 has a left side 930 and a right side 935. A left strap loop 240 may be mounted on the left side 930 and a right strap loop 245 may be mounted on the right side 935. A refill cap 330 may be located on the top surface 940 of the housing 200.

The water reservoir 300 located within the housing 200 is a container for the water 900 that will be sprayed as the mist 910 during the night. The shape of the water reservoir 300 follows the contours of the housing 200. At the rear point 925 of the housing 200, the water reservoir 300 may narrow to form a fluid pickup valley 915. The fluid pickup valley 915 may allow the water 900 to collect at the entrance of an intake tubing 310. The water reservoir 300 may be refilled by opening the refill cap 330. In a preferred embodiment, the water reservoir 300 has a capacity of 80 cc to 120 cc.

The one or more spray nozzles 220 point from the housing 200 into the mouth 960 of the user 950. Specifically, when the invention 100 is in place on the user 950, the one or more spray nozzles 220 may be positioned to spray the mist 910 under a tongue 965 of the user 950. The one or more spray nozzles 220 may atomize the water 900, which has been pressurized by the finger pump 320 so that the mist 910 may be delivered into the mouth 960 of the user 950.

The one or more teeth clips 210 hold the housing 200 in place while the invention 100 is being used. Specifically, the one or more teeth clips 210 may slip over one or more lower front teeth 980 of the user 950. Because the one or more teeth clips 210 may at least partially surround the one or more lower front teeth 980, the one or more teeth clips 210 may prevent the housing 200 from sliding from side to side. The one or more teeth clips 210, in conjunction with a strap 250, may also prevent the housing 200 from pulling out of the mouth 960 of the user 950. The one or more teeth clips 210 may prevent the housing 200 from moving down. A combination of the strap 250, the tongue 965 of the user 950 and an upper lip 975 of the user 950 may prevent the housing 200 from lifting up.

The valve 340 may allow the water 900 to pass from the intake tubing 310 to one or more nozzle tubes 230 when the valve 340 is in an OPEN state. The valve 340 may prevent the water 900 from passing from the intake tubing 310 to the one or more nozzle tubes 230 when the valve 340 is in a CLOSED state. The OPEN or CLOSED state of the valve 340 may be determined via the valve timer 350.

The valve timer 350 may be a wind-up, mechanical timing component. Energy to drive the valve timer 350 may be provided by the user 950 turning a timer fob 355 located on the left side 930 of the housing 200 or on the right side 935 of the housing 200. The energy may be stored in a spring (not shown in the figures). The energy stored in the spring may cause a timer shaft 365 to rotate slowly. In a preferred embodiment, the timer shaft 365 may rotate for a period of 4 to 12 hours when the valve timer 350 is fully wound. At recurring intervals during the rotation of the timer shaft 365, the timer shaft 365 may place the valve 340 into the OPEN state for a first duration of time and the timer shaft 365 may then place the valve 340 into a CLOSED state for a second duration of time. In a preferred embodiment, the first duration of time when the valve 340 is in the OPEN state will last long enough for the invention 100 to deliver 0.75 cc+/−20% of the water 900 through the one or more spray nozzles 220. In a preferred embodiment, the second duration of time when the valve 340 is in the CLOSED state will last for 20 minutes+/−20%. The timer shaft 365 may be located within the housing 200 but outside of the water reservoir 300.

The finger pump 320 may be used to pump air into the water reservoir 300 so that the water 900 in the water reservoir 300 is pressurized. The increased pressure created by using the finger pump 320 may force the water 900 in the water reservoir 300 to enter the intake tubing 310 and to move through the intake tubing 310, the valve 340, the one or more nozzle tubes 230, and the one or more spray nozzles 220. The finger pump 320 may comprise a one-way air valve (not shown in the figures) so that neither air nor water can escape through the finger pump 320. The finger pump 320 may be located within the water reservoir 300, but outside of the water reservoir 300. The finger pump 320 may be accessible on the top surface 940 of the housing 200 so that the user 950 may use the finger pump 320 to create internal pressure. The finger pump 320 may connect directly to the water reservoir 300 to force air into the water reservoir 320.

A valve release 360 may override the action of the valve timer 350 and may force the valve 340 to the OPEN state. The valve release 360 may be provided to aid in the draining and cleaning of the water reservoir 300. The valve release 360 may be accessible via the top surface 940 of the housing 200.

The one or more nozzle tubes 230 may connect between the one or more spray nozzles 220 and the valve 340. The one or more nozzle tubes 230 may direct the water 900 from the valve 340 to the one or more spray nozzles 220. The one or more nozzle tubes 230 may be located within the housing 200 but outside of the water reservoir 300.

The intake tubing 310 directs the water 900 from the fluid pickup valley 915 to the valve 340. The intake tubing 310 may be located within the housing 200. One end of the intake tubing 310 may lie outside of the water reservoir 300 and this end may connect to the valve 340. The intake tubing 310 may pass through a wall of the water reservoir 300. The hole in the wall of the water reservoir 300 where the intake tubing 310 passes through will be sealed to prevent the water 900 from leaking. The end of the intake tubing 310 that is inside of the water reservoir 300 may terminate at the fluid pickup valley 915.

The left strap loop 240 and the right strap loop 245 may provide an attachment point for the strap 250. The strap 250 may be a flexible, detachable strip may be used to hold the invention 100 in place while the user 950 sleeps. Specifically, the strap 250 may pass around a head 970 of the user 950 to prevent the invention 100 from pulling out of the mouth 960 of the user 950. One end of the strap 250 may attach to the left strap loop 240 on the left side 930 of the housing 200 and the other end of the strap 250 may attach to the right strap loop 245 on the right side 935 of the housing 200.

With respect to the above description, it is to be realized that the optimum dimensional relationship for the various components of the invention described above and in FIGS. 1 through 4, include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

The inventor claims:

1. A saliva management system comprising:
a housing, a water reservoir, one or more spray nozzles, one or
more teeth clips, a valve, a valve timer, and a finger pump;
wherein the saliva management system is adapted to be worn by a user while sleeping;
wherein the saliva management system is adapted to periodically spray a mist of water into a mouth of the user;
wherein the housing defines an enclosure for the saliva management system;
wherein the housing has a front side which is adapted to contact with the mouth of the user;
wherein the one or more spray nozzles and the one or more teeth clips are mounted on the front side of the housing;
wherein the housing has a top surface and a bottom surface;
wherein both the top surface and the bottom surface curve downward as they progress towards a rear point of the housing;
wherein the housing has a maximum top-to-bottom thickness at the front side of the housing of no more than 50 mm;
wherein the top-to-bottom thickness narrows at the rear point.

2. The saliva management system according to claim 1
wherein the housing has a left side and a right side;
wherein a left strap loop is mounted on the left side;
wherein a right strap loop is mounted on the right side;
wherein a refill cap is located on the top surface of the housing.

3. The saliva management system according to claim 2
wherein the water reservoir located within the housing is a container for the water that will be sprayed as the mist during the night;
wherein the shape of the water reservoir follows the contours of the housing;
wherein the rear point of the housing, the water reservoir narrows to form a fluid pickup valley;
wherein the fluid pickup valley allows the water to collect at the entrance of an intake tubing;
wherein the water reservoir is refilled by opening the refill cap.

4. The saliva management system according to claim 3
wherein the water reservoir has a capacity of 80 cc to 120 cc.

5. The saliva management system according to claim 3
wherein the one or more spray nozzles are adapted to point from the housing into the mouth of the user;
wherein the one or more spray nozzles are adapted to spray the mist under a tongue of the user;
wherein the one or more spray nozzles atomize the water which has been pressurized by the finger pump.

6. The saliva management system according to claim 5
wherein the one or more teeth clips hold the housing in place while the saliva management system is being used;
wherein the one or more teeth clips are adapted to slip over one or more lower front teeth of the user;
wherein the one or more teeth clips prevent the housing from sliding from side to side;
wherein the one or more teeth clips, in conjunction with a strap, are adapted to prevent the housing from pulling out of the mouth of the user;
wherein the one or more teeth clips prevent the housing from moving down.

7. The saliva management system according to claim 6
wherein the valve allows the water to pass from the intake tubing to one or more nozzle tubes when the valve is in an OPEN state;
wherein the valve prevents the water from passing from the intake tubing to the one or more nozzle tubes when the valve is in a CLOSED state;
wherein the OPEN or CLOSED state of the valve is determined by the valve timer.

8. The saliva management system according to claim 7
wherein the valve timer is a wind-up, mechanical timing component;
wherein energy to drive the valve timer is provided by turning a timer fob located on the left side of the housing or on the right side of the housing;
wherein the energy is stored in a spring;
wherein the energy stored in the spring causes a timer shaft to rotate.

9. The saliva management system according to claim 8
wherein the timer shaft rotates for a period of 4 to 12 hours when the valve timer is fully wound;
wherein at recurring intervals during the rotation of the timer shaft, the timer shaft places the valve into the OPEN state for a first duration of time and the timer shaft then places the valve into a CLOSED state for a second duration of time;
wherein the timer shaft is located within the housing but outside of the water reservoir.

10. The saliva management system according to claim 9
wherein the first duration of time when the valve is in the OPEN state will last long enough for the saliva management system to deliver 0.75 cc+/−20% of the water through the one or more spray nozzles.

11. The saliva management system according to claim 9
wherein the second duration of time when the valve is in the CLOSED state will last for 20 minutes+/−20%.

12. The saliva management system according to claim 9
wherein the finger pump is used to pump air into the water reservoir so that the water in the water reservoir is pressurized;
wherein the increased pressure created by using the finger pump forces the water in the water reservoir to enter the intake tubing and to move through the intake tubing, the valve, the one or more nozzle tubes, and the one or more spray nozzles;
wherein the finger pump comprises a one-way air valve;
wherein the finger pump is located within the water reservoir but outside of the water reservoir;
wherein the finger pump is accessible on the top surface of the housing;
wherein the finger pump connects to the water reservoir to force air into the water reservoir.

13. The saliva management system according to claim 12
wherein a valve release overrides the action of the valve timer and forces the valve to the OPEN state;
wherein the valve release is provided to aid in the draining and cleaning of the water reservoir;
wherein the valve release is accessible via the top surface of the housing.

14. The saliva management system according to claim 13
wherein the one or more nozzle tubes connects between the one or more spray nozzles and the valve;
wherein the one or more nozzle tubes directs the water from the valve to the one or more spray nozzles;
wherein the one or more nozzle tubes are located within the housing but outside of the water reservoir.

15. The saliva management system according to claim 14
wherein the intake tubing directs the water from the fluid pickup valley to the valve;
wherein the intake tubing is located within the housing;
wherein one end of the intake tubing lies outside of the water reservoir and this end connects to the valve;
wherein the end of the intake tubing that is inside of the water reservoir terminates at the fluid pickup valley.

16. The saliva management system according to claim 15
wherein the left strap loop provides an attachment point for the strap;
wherein the right strap loop provides an attachment point for the strap;
wherein the strap is a flexible strip that is used to hold the saliva management system in place;
wherein the strap is detachable;
wherein the strap is adapted to pass around a head of the user to prevent the saliva management system from pulling out of the mouth of the user;
wherein one end of the strap attaches to the left strap loop on the left side of the housing;
wherein the other end of the strap attaches to the right strap loop on the right side of the housing.

* * * * *